(12) United States Patent
Zhang et al.

(10) Patent No.: US 9,770,193 B2
(45) Date of Patent: Sep. 26, 2017

(54) DETECTING APPARATUS FOR CURVED SURFACE OF SOLE AND DISTRIBUTION OF PRESSURE THEREON

(71) Applicants: Tianchang Zhang, Foshan (CN); Caihong Huo, Foshan (CN)

(72) Inventors: Tianchang Zhang, Foshan (CN); Caihong Huo, Foshan (CN)

(*) Notice: Subject to any disclaimer, the term of this patent is extended or adjusted under 35 U.S.C. 154(b) by 35 days.

(21) Appl. No.: 14/759,342

(22) PCT Filed: Dec. 27, 2013

(86) PCT No.: PCT/CN2013/090711
§ 371 (c)(1),
(2) Date: Jul. 6, 2015

(87) PCT Pub. No.: WO2014/106442
PCT Pub. Date: Jul. 10, 2014

(65) Prior Publication Data
US 2015/0335270 A1  Nov. 26, 2015

(30) Foreign Application Priority Data
Jan. 5, 2013 (CN) .................... 2013 2 0005147 U

(51) Int. Cl.
*A61B 5/107* (2006.01)
*A61B 5/00* (2006.01)
(Continued)

(52) U.S. Cl.
CPC ............ *A61B 5/1074* (2013.01); *A43D 1/022* (2013.01); *A61B 5/1036* (2013.01);
(Continued)

(58) Field of Classification Search
CPC .............................. A61B 5/1074; G01B 5/207
See application file for complete search history.

(56) References Cited

U.S. PATENT DOCUMENTS

| | | | |
|---|---|---|---|
| 2009/0183388 A1* | 7/2009 | Miller | .................... A43B 7/141 36/43 |
| 2010/0106061 A1 | 4/2010 | Lott et al. | |

(Continued)

FOREIGN PATENT DOCUMENTS

| | | |
|---|---|---|
| CN | 2549903 | 5/2003 |
| CN | 2564987 | 8/2003 |

(Continued)

OTHER PUBLICATIONS

Ye Bin, CN 2564987 Y, Aug. 2003, ProQuest Machine Translation.*

*Primary Examiner* — Devin Henson
*Assistant Examiner* — Benjamin Melhus
(74) *Attorney, Agent, or Firm* — The Farrell Law Firm, P.C.

(57) ABSTRACT

A detecting apparatus for curved surface of sole and distribution of pressure thereon, that includes a housing, a top plate enclosed at an opening of the housing, a detecting mechanism capable of vertical reciprocating movement and contacting the curved surface of sole, a detecting circuit collecting the vertical movement data of the detecting mechanism and transferring the vertical movement data to a data processing system, and the data processing system receiving and analyzing the data as well as re-constructing the profile of sole. The detection and reconstruction for 3D surface of the sole and pressure distribution thereon can be achieved by emitting and receiving an infrared ray, with high precision, strong anti-jamming ability, low power consumption and low cost.

3 Claims, 3 Drawing Sheets

(51) Int. Cl.
*A61B 5/103* (2006.01)
*G01B 11/24* (2006.01)
*A43D 1/02* (2006.01)

(52) U.S. Cl.
CPC ............ *A61B 5/7271* (2013.01); *G01B 11/24* (2013.01); *A61B 5/742* (2013.01)

(56) References Cited

U.S. PATENT DOCUMENTS

2010/0286951 A1* 11/2010 Danenberg ........... A61B 5/1074
  702/172
2012/0107584 A1* 5/2012 Eibon ................. C09B 67/0033
  428/212

FOREIGN PATENT DOCUMENTS

| CN | 2564987 Y * | 8/2003 |
| CN | 103006233 | 4/2013 |
| CN | 203263396 | 11/2013 |

* cited by examiner

DETECTING APPARATUS FOR CURVED SURFACE OF SOLE AND DISTRIBUTION OF PRESSURE THEREON

PRIORITY

This application is a National Phase Entry of PCT International Application No. PCT/CN2013/090711, which was filed on Dec. 27, 2013, and claims priority to Chinese Patent Application No. 201320005147.0, which was filed on Jan. 5, 2013, the contents of each of which are incorporated herein by reference.

TECHNICAL FIELD

The invention relates to a detecting apparatus for curved surface of the sole of the foot, which belongs to the field of the detecting equipment for foot health in humans, in particular a detecting apparatus for curved surface of sole and distribution of pressure thereon.

BACKGROUND

Currently there are the following methods for detecting the sole.

1. Moulding method: a mould of sole is made of parget or any other suitable plastic materials, by coating the materials over the sole. However, the mould lacks the digital data about the sole, and provides few information with low precision. The method can only be used for qualitative analysis and applications.

2. Scanning method: There are two scanning methods, i.e. scanning the sole without pressure thereon, and scanning the sole under pressure thereon. The former method is performed when the foot is hanging naturally, and the latter method is performed when the foot is stepping on a transparent glass. In both methods, the sole can be scanned by using the laser-scanning method, whereby the profile information of the sole can be obtained. However the measured information is a limited data because no pressure, or no fully pressure is applied on the sole. In addition, these methods are operated complicated with high cost, which were not often utilized.

3. Plane imaging method: 3D surface image with grid projection is obtained by CCD or other plane imaging methods, and the information of the 3D surface may be calculated based on the deformation of the grids. Although the method costs less and achieves an high resolution ratio of the sampled data, the deformation of the data may be too much, and the 3D gradient is limited by the angle of illumination to the grids. Thus the application of the method is also limited.

4. Inductance/capacitance method: when the planar materials are deformed, the inductance and/or capacitance thereon will vary, thus the curved surface can be measured by measuring the inductance and/or capacitance. However, the method has a low precision and a low antijamming ability, so that the method is unpractical.

5. Grating method: the surface to be detected is arranged as a grating matrix. During the detection, a displacement of 3D surface orthogonal to the grating matrix is recorded by the grating matrix, and thereby the information of 3D surface can be obtained. However, grating sensors usually have a big size, such that they might not be able to be arranged in a certain area, whereby the resolution ratio of the detection is reduced and the transmission mechanism is also complicated. The grating output is frequency signal, which requires a rapid response of the signal detection system in the grating matrix, as well as an excellent hardware/circuit. The method has a low resolution ratio and high cost.

6. Photoelectric reflex scanning method: the surface to be detected is arranged as a reflective phototube matrix. The phototubes receive reflected signals from detecting mechanism. The detecting mechanism is connected to the surface to be detected, such that the reflected signals vary upon the deformation of the curved surface. Although the method is easy and practical, there is no linear relationship between the reflected signals and the deformation/displacement, the dispersion between the components would be high such that it is difficult to achieve the standardization of the system.

SUMMARY OF THE INVENTION

To overcome the above problems, the invention provides a detecting apparatus for curved surface of sole and distribution of pressure thereon, having a simple construction, a good linear and consistent performance, being able to achieve a 3D reconstruction of curved surface of sole.

The invention is achieved by the following solution:

A detecting apparatus for curved surface of sole and distribution of pressure thereon, comprises a housing, a top plate enclosed at an opening of the housing, a detecting mechanism capable of vertical reciprocating movement and contacting the curved surface of sole, a detecting circuit collecting the vertical movement data of the detecting mechanism and transferring the vertical movement data to a data processing system, and the data processing system receiving, analyzing the data as well as re-constructing the profile of sole.

Further, the detecting mechanism comprises several column matrix for one's foot tread, several sensor rod matrix for detection and a guide plate, wherein the column matrix is installed on the top plate, and comprises a number of supporting columns arranged in matrix and capable of vertical movement; the sensor rod matrix is installed beneath the top plate, and comprises a number of sensor rod units arranged in matrix and each corresponding to each supporting column; and the guide plate is configured inside the housing and remains a distance from the top plate, having several aperture matrix wherein each aperture corresponds to each sensor rod unit.

Further, each sensor rod unit comprises a contact tip, a rod and a reset spring, wherein the contact tip is configured at the top end of the rod and contacted and cooperated with the supporting column; a lower end of the rod is movably configured through the aperture of the guide plate, and a bottom of the rod is provided with a translucent film; and the return spring sheathed the rod, both ends of the spring contact with the contact tip and an upper surface of the guide plate respectively.

Further, the detecting circuit comprises a scanning module for scanning a varied displacement of the sensor rod matrix, an infrared ray emission module for converting electric power of the scanning module to luminous energy and transmitting the luminous energy to an infrared ray receiving module through the translucent film, the infrared ray receiving module for converting the luminous energy from the infrared ray emission module to electric power, an analog-digital (A/D) converting module for converting the voltage analog signals from the infrared ray receiving module to digital signals, and a microprocessing module for transforming the digital signals to displacement data which would then be transmitted to the data processing system.

Further, the invention also comprises a photoelectric conversion module, for converting the electric power to the luminous energy and vice versa.

Further, the microprocessing module is provided with a USB interface connected to the data processing system.

Further, the data processing system comprises a data collection and analysis module for receiving and analyzing the displacement data from the microprocessing module, a 3D surface reconstruction module for reconstructing the curved surface after the analysis of the displacement data and displaying a 2D contour map or a 3D perspective view, and a data classification and management module for classifying, storing and managing processed data.

Compared with the prior art, the benefits of the present invention are that:

1. The detection and reconstruction for 3D surface of the sole and pressure distribution thereon can be achieved by emitting and receiving an infrared ray, with high precision, strong antijamming ability, low power consumption and low cost;

2. The overall construction of the present invention is simple and practical, and the present invention has a good linear and consistent performance, which can be operated easily and used widely.

For better understanding the present invention, a specific embodiment is described hereinafter with reference to accompanying drawings.

DETAILED DESCRIPTION OF THE INVENTION

Figure 1:
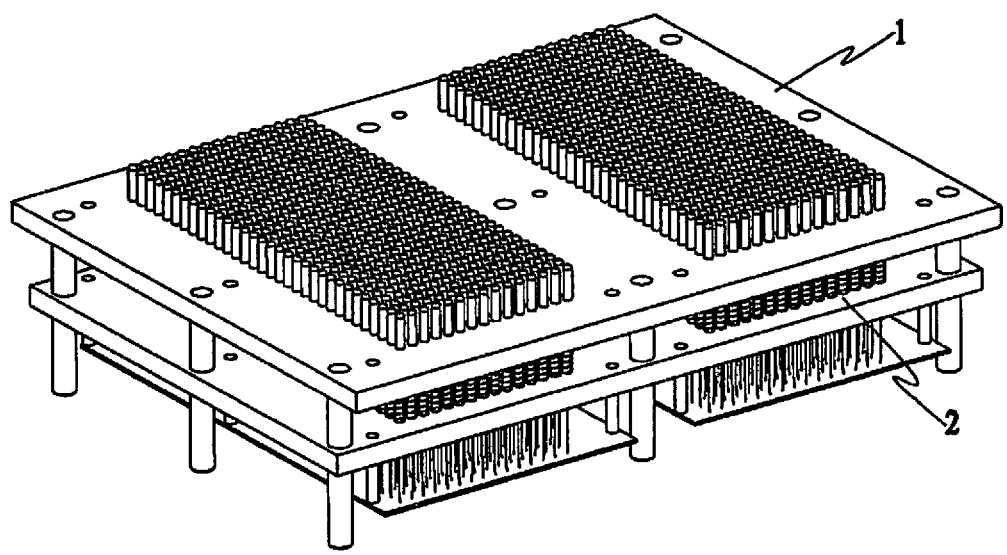
FIG. 1 shows a schematic view of an assembly according to the invention.
Figure 2:
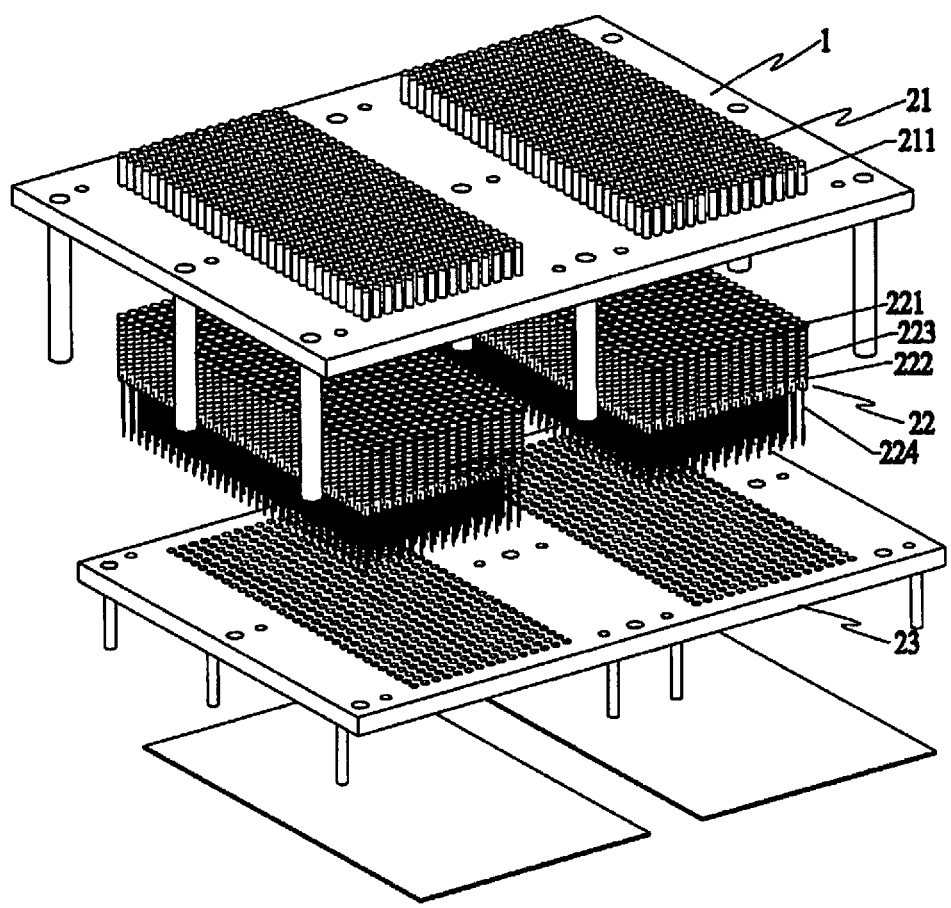
FIG. 2 shows an explosive view of the assembly shown in FIG. 1.

As shown in FIGS. 1 & 2, a detecting apparatus for curved surface of sole and distribution of pressure thereon according to the invention, comprises a housing, a top plate 1 enclosed at an opening of the housing, a detecting mechanism 2 capable of vertical reciprocating movement and contacting the curved surface of sole, a detecting circuit collecting the vertical movement data of the detecting mechanism 2 and transferring the vertical movement data to a data processing system, and the data processing system receiving, analyzing the data as well as re-constructing the profile of sole.

The detecting mechanism 2 comprises several column matrix 21 for one's foot tread, several sensor rod matrix 22 for detection and a guide plate 23, wherein the column matrix 21 is installed on the top plate 1, and comprises a number of supporting columns 211 arranged in matrix and capable of vertical movement; the sensor rod matrix 22 is installed beneath the top plate 1, and comprises a number of sensor rod units arranged in matrix and each corresponding to each supporting column 211; and the guide plate 23 is configured inside the housing and remains a distance from the top plate 1, having several aperture matrix wherein each aperture corresponds to each sensor rod unit.

Further, each sensor rod unit comprises a contact tip 221, a rod 222 and a reset spring 223, wherein the contact tip 221 is configured at the top end of the rod 222 and contacted and cooperated with the supporting column 211; a lower end of the rod 222 is movably configured through the aperture of the guide plate 23, and a bottom of the rod 222 is provided with a translucent film 224 which is inserted into the circuit board of the detecting circuit; and the return spring 223 sheathed the rod 222, both ends of the spring 223 contact with the contact tip 221 and an upper surface of the guide plate 23 respectively.

The detecting circuit comprises a scanning module for scanning a varied displacement of the sensor rod matrix, an infrared ray emission module for converting electric power of the scanning module to luminous energy and transmitting the luminous energy to an infrared ray receiving module through the translucent film, the infrared ray receiving module for converting the luminous energy from the infrared ray emission module to electric power, an analog-digital (A/D) converting module for converting the voltage analog signals from the infrared ray receiving module to digital signals, and a microprocessing module for transforming the digital signals to displacement data which would then be transmitted to the data processing system.

Further, the embodiment also comprises a photoelectric conversion module, for converting the electric power to the luminous energy and vice versa; and the microprocessing module is provided with a USB interface connected to the data processing system.

The data processing system comprises a data collection and analysis module for receiving and analyzing the displacement data from the microprocessing module, a 3D surface reconstruction module for reconstructing the curved surface after the analysis of the displacement data and displaying a 2D contour map or a 3D perspective view, and a data classification and management module for classifying, storing and managing processed data.

Figure 3:
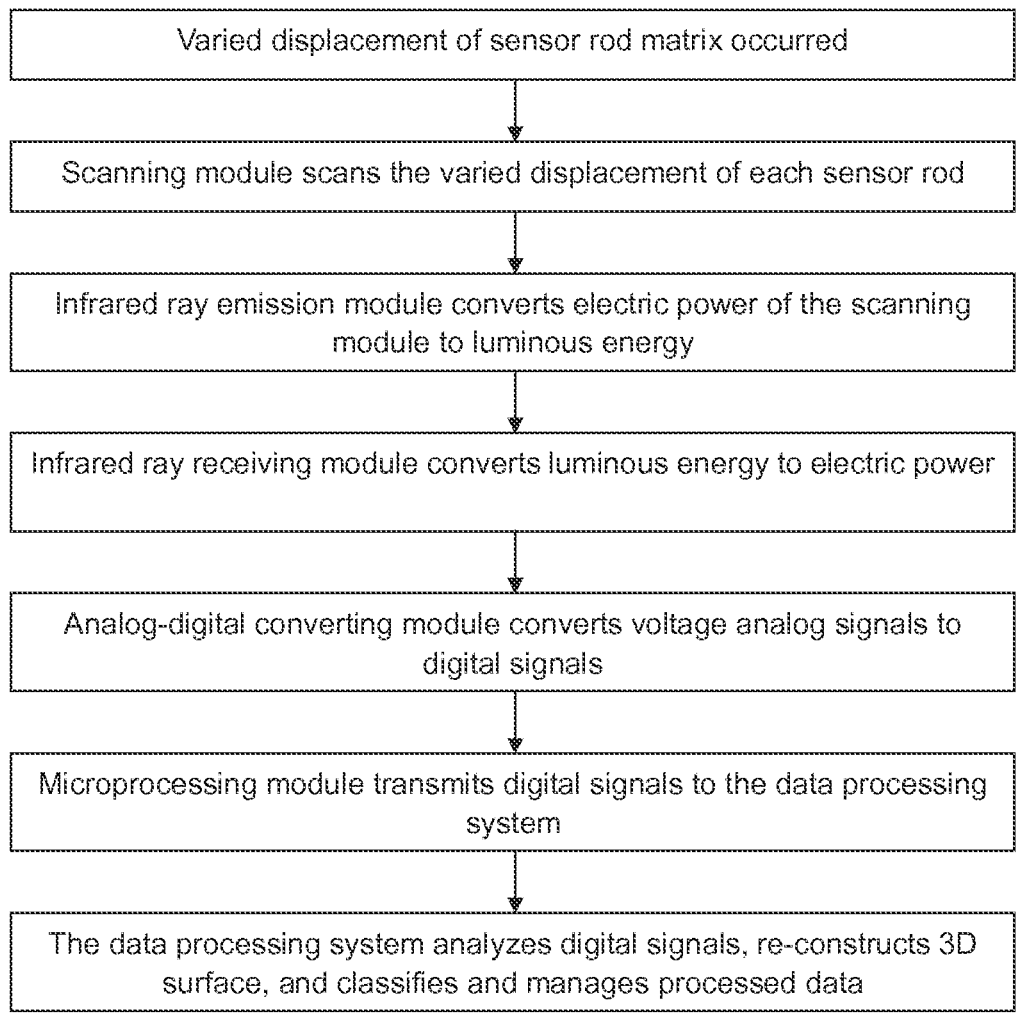
FIG. 3 shows an operation flowchart according to the invention.

As shown in FIG. 3, the work principle of the present invention is as follows:

During detection, one stands on the column matrix 21 without shoes, the human weight drives the column matrix 21 and the corresponding sensor rods moving downwards, the displacement data of the sensor rods are thus generated by the contact tips 221. Afterwards, the scanning module scans the varied displacement of each rod in the sensor rod matrix 22, and the infrared ray emission module converts the electric power of the scanning module to luminous energy. The luminous energy is received by the infrared ray receiving module through the translucent film 224, and converted to electric power, whereby the varied displacement of the sensor rod matrix 22 can be indicated by the electric power due to varied grayscale of the translucent film 224, then the voltage analog signals from the infrared ray receiving module are converted to digital signals by the analog-digital converting module. The digital signals are transferred to the data processing system via the USB interface, and thereby classified, stored and managed. Thereby the detection and reconstruction for 3D curved surface of sole are accomplished.

The embodiment described hereinbefore is merely preferred embodiment of the present invention and not for purposes of any restrictions or limitations on the invention. It will be apparent that any non-substantive, obvious alterations or improvement by the technician of this technical field according to the present invention may be incorporated into ambit of claims of the present invention.

The invention claimed is:

1. A detecting apparatus for a curved surface of sole and configured to distribute pressure thereon, the apparatus comprising:

a housing;

a top plate enclosed at an opening of the housing;

a detecting mechanism configured to reciprocate vertically and contact the curved surface of sole; and a detecting circuit configured to collect vertical movement data of the detecting mechanism and transfer the vertical movement data to a data processing system, wherein the detecting mechanism comprises a column matrix, a sensor rod matrix, and a guide plate, in which:

the column matrix is installed on the top plate;

the sensor rod matrix is installed beneath the top plate, and comprises a plurality of sensor rod units arranged in matrix form, with each sensor rod of the plurality of sensor rod units corresponding to a supporting column; and the guide plate is configured inside the housing, separated by a distance from the top plate, and having several aperture matrices wherein each aperture corresponding to each sensor rod unit of the plurality of sensor rod units, wherein each sensor rod unit of the plurality of sensor rod units comprises:

a contact tip, a rod, and a reset spring, in which:

the contact tip is configured at a top end of the sensor rod unit, and contacted and cooperated with a respective supporting column, a lower end of the sensor rod unit is movably configured through the aperture of the guide plate, and a bottom of the sensor rod unit is provided with a translucent film with varied grayscale; and the reset spring sheathes the sensor rod unit, and respective ends of the reset spring contact with the contact tip and an upper surface of the guide plate, and wherein the detecting circuit comprises:

a scanner configured to scan a varied displacement of the sensor rod matrix;

a photoelectric converter configured to convert electric power to luminous energy, an infrared ray emitter configured to convert electric power of the scanner to luminous energy, and transmit the luminous energy that penetrates the translucent film to an infrared ray receiver through the translucent film, the infrared ray receiver configured to convert the luminous energy from the infrared ray emitter to electric power, an analog-digital converter configured to convert the voltage analog signals from the infrared ray receiver to digital signals, and a microprocessor configured to transform the digital signals to displacement data which would then be transmitted to the data processing system.

2. The detecting apparatus according to claim 1, wherein the microprocessor is provided with a USB interface connected to the data processing system.

3. The detecting apparatus according to claim 1, wherein the data processing system comprises a data analyzer configured to receive and analyze the displacement data from the microprocessor;

a 3D surface reconstructer configured to reconstruct the curved surface after the analysis of the displacement data, and control display of a 2D contour map or a 3D perspective view; and a data manager configured to classify, store and manage processed data.

* * * * *